United States Patent [19]

Hoffman

[11] Patent Number: 5,525,630
[45] Date of Patent: Jun. 11, 1996

[54] TREATMENT FOR CARBON MONOXIDE POISONING

[75] Inventor: Stephen J. Hoffman, Englewood, Colo.

[73] Assignee: Allos Therapeutics, Inc., Denver, Colo.

[21] Appl. No.: 457,580

[22] Filed: Jun. 1, 1995

[51] Int. Cl.⁶ ..................................................... A61K 31/19
[52] U.S. Cl. ............................................................ 514/563
[58] Field of Search ............................................. 514/563

[56] References Cited

U.S. PATENT DOCUMENTS 4,921,997  5/1990  Lalezari et al. .................. 514/563

OTHER PUBLICATIONS

Lalezari et al., Biochemistry, 29:1515–1523 (1990).

*Primary Examiner*—Phyllis G. Spivack
*Attorney, Agent, or Firm*—Whitham, Curtis, Whitham, & McGinn

[57] ABSTRACT

Allosteric hemoglobin modifier compounds are disclosed that clear carbon monoxide hemoglobin from a host animal.

1 Claim, 1 Drawing Sheet

TREATMENT FOR CARBON MONOXIDE POISONING

BACKGROUND OF THE INVENTION

1. Field of the Invention

The invention is generally related to a new use for allosteric hemoglobin modifier compounds in the treatment of carbon monoxide poisoning.

2. Description of the Prior Art

Carbon monoxide is a colorless, odorless, flammable, toxic gas. Carbon monoxide is the most widely spread gaseous hazard to which man is exposed. The toxicity of carbon monoxide is a result of its reaction with the hemoglobin of blood. CO binds to hemoglobin, displaces oxygen and leads to asphyxiation. To date, there is no good treatment modality for assisting patients to clear carbon monoxide from their blood streams other than breathing oxygen.

SUMMARY OF THE INVENTION

It is an object of this invention to provide a method for treating carbon monoxide exposure.

According to the invention, allosteric hemoglobin modifier compounds have been found to enhance the rate carbon monoxide is cleared from the body of a patient.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
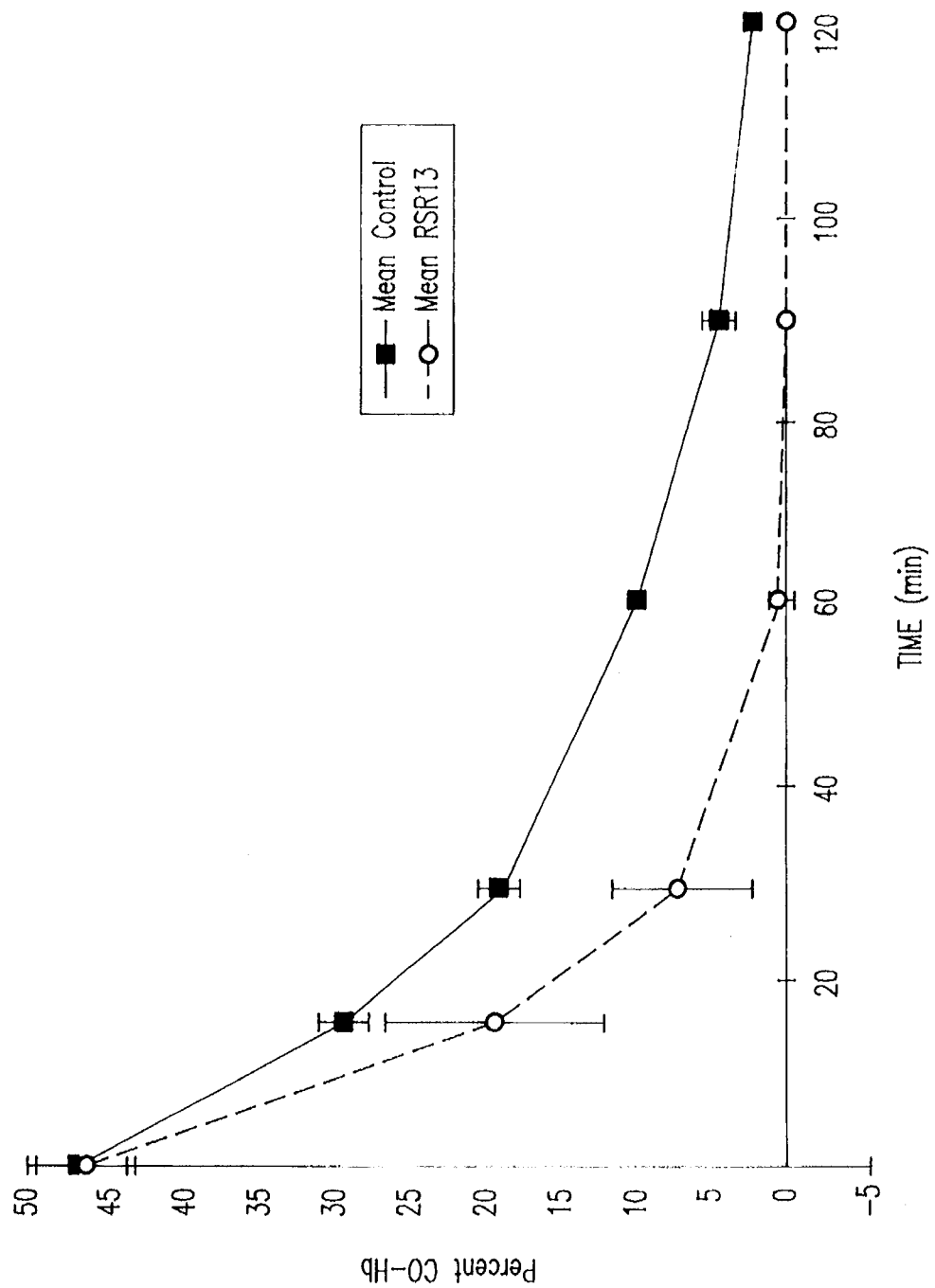
FIG. 1 is a graph showing the comparative results of untreated rats and rats treated with an allosteric hemoglobin modifier compound in terms of the ability of the rats to clear CO-Hb from their bloodstreams.

Carbon monoxide exposure and clearing experiments were conducted with male Sprague Dawley rats available from Charles River, Portage, Mich. Eight rats, all weighing approximately 300 grams, were provided with identification, and quarantined for five days prior to exposure to sub-lethal levels of carbon monoxide. The quarantine period was used to acclimate the animals prior to the study. The animals were handled according to the directives set forth by the Department of Health and Human Services (DHHS) in the *Guide for the Care and Use of Laboratory Animals*. Specifically, the rats were housed separately from all other species in stainless steel, wire mesh bottom cages, they were kept in an animal room with a controlled climate (64°–79° F., 40–70% relative humidity, 12/12 hour light/dark cycle), potable water and certified rodent feed was provided ad libitum throughout the acclimation and study period except for the night prior to blood collection and/or necropsy, and the rats received 100% fresh air thoughout the study.

After the five day acclimation period, the animals were exposed to 1000 ppm CO by introducing a CO/air mix into a chamber in which the animals were positioned under positive pressure for one hour. The time period of exposure was selected to achieve a sub-lethal, circulating CO-Hb level of approximately 40% in each of the rats.

After treatment with CO, the animals were split randomly into two groups and exposed to room air. The control group received a 0.45% saline vehicle, and the treated group received the 0.45% saline vehicle and a dose of 400 mg/kg body weight 2-[4-((((3,5-dimethylphenyl)amino)carbonyl)methyl) phenoxy]-2-methyl propionic acid, which is referred to as RSR-13. In both groups, a total of 5 ml/kg body weight was delivered by intravenous injection into the caudal vein at a rate of approximately 2 ml/min. The intravenous route was selected for the study since it is the most likely delivery route for treating human exposure. Table I sets forth the dosing schedule for each of the groups.

TABLE 1

| Group | Dose Level (mg/kg) | Dose Volume (ml/kg) | No. of rats |
|---|---|---|---|
| Control (saline) | 0 | 5 | 4 |
| Treated (RSR-13 + saline) | 400 | 5* | 4 |

*80 mg RSR-13/ml

To evaluate carbon monoxide clearing, serial blood draws will be made at 0, 15, 30, 60, 90, and 120 minutes after treatment with saline or RSR-13 and saline. Blood samples were obtained by sinus puncture. These samples were then analyzed for CO-Hb by co-oximetry.

FIG. 1 shows that the CO-Hb is cleared from the treated rats in approximately one hour, whereas the control rats had CO-Hb remaining even after two hours exposure to fresh air. In addition, the rat of CO-Hb clearing in the first thirty minutes was significantly higher in the treated rats than in the control rats. Thus, RSR-13 has significant therapeutic potential in treating carbon monoxide poisoning.

While the experiments were conducted with RSR-13, other allosteric hemoglobin modifier compounds which right-shift the oxygen dissociation curve and cause hemoglobin to bind oxygen and carbon monoxide less tightly may also be used within the practice of this invention. In addition, RSR-13 it should be understood that is a model compound for the class of allosteric hemoglobin modifier compounds having the structural formula:

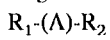

where $R_1$ and $R_2$ each are a substituted or unsubstituted aromatic or heteroaromatic compound, or a substituted or unsubstituted alkyl or heteroalkyl ring compound, or a substituted or unsubstituted phthalimide compound, and where $R_1$ and $R_2$ may be the same or different, where A is a chemical bridge which includes 2–4 chemical moieties bonded together betwen $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound fromed with $R_1$ or $R_2$, $CH_2$, CH, and C, and where at least one of $R_1$ and $R_2$ is substituted with a compound having the chemical formula:

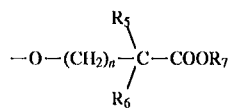

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moities may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group. Thus, any compound fitting this description should be useful in the practice of this invention due to their allosteric activity with the hemoglobin molecule. Synthesis of the allosteric hemogobin modifier compounds of the present invention is described in detail in U.S. Pat. Nos. 5,290,803, 5,122,539, and U.S. Ser. No. 08/101,501 filed Jul. 30, 1993 (issue fee paid), and each of these documents is incorporated herein by reference.

The dose of the allosteric hemoglobin modifier compound will depend on a number of parameters including the CO-Hb concentration in the CO poisoned patient (human or animal), the age and sex of the patient, and the route of delivery (oral, i.v., i.p., aerosol spray). In any case, a sufficient quantity of the allosteric hemoglobin modifier compound should be provided to quickly lower the CO-Hb concentration in the patient.

In the experiment noted above, saline solution was used as the injectable vehicle, and the RSR-13 compound. However, it should be understood that any injectable vehicle in which RSR-13 or other allosteric hemoglobin modifier compounds can be dissolved or dispersed could be used within the practice of this invention. Suitable examples include oils, fat emulsions, suspensions, liposomes, lipid vesicles, etc., where the terms lipid, phospholipid, and fat can be used interchangeably.

While the invention has been described in terms of its preferred embodiments, those skilled in the art will recognize that the invention can be practiced with modification within the spirit and scope of the appended claims.

I claim:

1. A method for treating patients exposed to carbon monoxide to rapidly clear carbon monoxide hemoglobin from the blood stream, comprising the steps of:

administering to a patient in need thereof a sufficient quantity of 2-[4-((((3,5-dimethylphenyl)amino) carbonyl)methyl)phenoxy]-2-methyl propionic acid to clear carbon monoxide hemoglobin from said patient's bloodstream; and allowing said patient to breath air after said step of administering.

* * * * *